(12) United States Patent
Danielmeier et al.

(10) Patent No.: US 6,391,161 B1
(45) Date of Patent: May 21, 2002

(54) METHOD FOR REDUCING THE CHLORINE CONTENT OF LOW MOLECULAR WEIGHT ISOCYANATES

(75) Inventors: Karsten Danielmeier, Bethel Park, PA (US); Dieter Mager, Leverkusen (DE); Reinhard Halpaap; Martin Brahm, both of Odenthal (DE); Eric Hoffman, Baytown, TX (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/532,584

(22) Filed: Mar. 22, 2000

(30) Foreign Application Priority Data

Mar. 30, 1999 (DE) .......................... 199 14 291

(51) Int. Cl.⁷ .......................... B01D 3/34; C07C 249/14
(52) U.S. Cl. .............. 203/6; 203/60; 203/91; 203/99; 203/100; 560/352
(58) Field of Search .............. 203/91, 100, 49, 203/43, 89, 60, 6, 33, 99; 560/336, 352; 210/634

(56) References Cited

U.S. PATENT DOCUMENTS

| | | | |
|---|---|---|---|
| 3,219,678 A | 11/1965 | Kober et al. ................ 260/453 |
| 3,264,336 A | 8/1966 | Powers ........................ 260/453 |
| 3,274,225 A | 9/1966 | Saunders et al. ........... 260/453 |
| 3,373,182 A | 3/1968 | Powers ........................ 260/453 |
| 3,423,486 A * | 1/1969 | Rätz et al. .................. 558/165 |
| 3,458,558 A | 7/1969 | Cheng ......................... 260/453 |
| 3,549,504 A | 12/1970 | Adica et al. ................. 203/49 |
| 3,759,971 A * | 9/1973 | Cuscurida et al. .......... 560/353 |
| 3,793,362 A | 2/1974 | Kolakowski et al. .. 260/453 SP |
| 3,799,963 A | 3/1974 | Adams .................. 260/453 SP |
| 3,840,578 A | 10/1974 | Hennig ................. 260/453 SP |
| 3,853,936 A | 12/1974 | Van Winkle .......... 260/453 SP |
| 3,857,871 A | 12/1974 | Hatfield, Jr. et al. ... 260/453 SP |
| 4,094,594 A * | 6/1978 | Blackwell ................... 560/353 |
| 4,094,894 A | 6/1978 | Blackwell .............. 260/453 SP |
| 4,294,666 A | 10/1981 | Astheimer et al. ............ 203/72 |
| 4,996,351 A | 2/1991 | Nafziger ..................... 560/352 |
| 5,386,054 A | 1/1995 | Scholl et al. ............... 560/352 |
| 5,498,740 A * | 3/1996 | Dermeik et al. .............. 558/89 |

FOREIGN PATENT DOCUMENTS

| | | |
|---|---|---|
| DE | 1138040 | 10/1962 |
| DE | 1950101 | 4/1971 |
| DE | 271820 | 9/1989 |
| DE | 285593 | 12/1990 |
| DE | 288594 | 4/1991 |
| DE | 288595 | 4/1991 |
| DE | 288596 | 4/1991 |
| DE | 288597 | 4/1991 |
| DE | 288598 | 4/1991 |
| DE | 288599 | 4/1991 |
| GB | 1034357 | 6/1966 |
| GB | 1080717 | 8/1967 |
| GB | 1111581 | 5/1968 |
| GB | 1112450 | 5/1968 |
| GB | 1186896 | 4/1970 |
| GB | 1229181 | 4/1971 |
| GB | 1347647 | 2/1974 |
| GB | 1362708 | 8/1974 |
| GB | 1384065 | 2/1975 |
| GB | 1458747 | 12/1976 |
| GB | 1459691 | 12/1976 |
| GB | 1517162 | 7/1978 |
| GB | 1570741 | 7/1980 |
| JP | 67004137 | 2/1967 |
| JP | 70010329 | 4/1970 |
| JP | 59088452 | 5/1984 |
| JP | 59108753 | 6/1984 |
| JP | 59172450 | 9/1984 |
| JP | 61161250 | 7/1986 |
| JP | 5058982 | 3/1993 |
| JP | 5163231 | 6/1993 |
| JP | 6345707 | 12/1994 |
| JP | 7278088 | 10/1995 |
| JP | 9323968 | 12/1997 |
| SU | 806677 | 5/1982 |
| ZA | 8100606 | 7/1982 |

OTHER PUBLICATIONS

DE 31085 38 Abstract, Reiff et al. Oct. 21, 1982.*

* cited by examiner

*Primary Examiner*—Virginia Manoharan
(74) *Attorney, Agent, or Firm*—Joseph C. Gil; Lyndanne M. Whalen; Carolyn M. Sloane

(57) ABSTRACT

An organic isocyanate or mixture of isocyanates is treated with at least one high molecular weight ester of phosphoric acid corresponding to a specified formula to remove chlorine compounds. The isocyanates which are purified in this manner are useful for the production of coatings, polyurethane moldings and chemical intermediates.

3 Claims, No Drawings

METHOD FOR REDUCING THE CHLORINE CONTENT OF LOW MOLECULAR WEIGHT ISOCYANATES

BACKGROUND OF THE INVENTION

This invention relates to a new method for purifying organic isocyanates or mixtures of isocyanates by reducing the content of chlorine compounds. In this method, an isocyanate is treated with a high molecular weight ester of phosphoric acid. The isocyanates which are purified in this manner are preferably used in coatings, polyurethane moldings and as intermediates.

Varying amounts of impurities present in isocyanates, which are due to the isocyanate production process, give rise to variations in the isocyanate activity. Variations in activity have an unfavorable effect on the reproducibility of products produced from these isocyanates, i.e. on the commercial value of these compounds. Thus, aromatic isocyanates such as the known phosgenation products of aniline-formaldehyde condensates, as well as 2,4- and 2,6-diisocyanatotoluene and aliphatic isocyanates such as isophorone diisocyanate contain a number of impurities of this type. These impurities are primarily compounds which contain chlorine and which give rise to variations in activity if these compounds contain "readily mobile" chlorine, or what is termed "hydrolyzable chlorine". Some of these hydrolyzable chlorine-containing compounds have proven to be relatively stable and they remain in the isocyanate(s) even after distillation. These stable chlorine compounds not only have an unfavorable effect on isocyanate activity but also have an unfavorable effect on the stability of the isocyanate. A uniform, lower content of these impurities, with the consequence of a standardized activity and enhanced ease of further processing of the isocyanate, is therefore important both technically and economically.

There have therefore been a number of investigations aimed at identifying options for the removal of chlorine compounds. There are a large number of patent applications which describe thermal methods for removing such chlorine compounds. For example, it is known that heating an isocyanate, particularly when stripping with an inert gas is employed at the same time, or heating of an isocyanate in an inert solvent under pressure while simultaneously removing volatile compounds under suction, reduces the content of readily separable chlorine compounds. See, e.g., DE-A 1,270,036; DD 271 820; U.S. Pat. No. 3,219,678; GB-A 1,080,717; DE-A 2,237,552; U.S. Pat. No. 3,857,871; U.S. Pat. No. 1,458,223; JP 0 727 808 8 A2; JP 0 634 570 7 A2; and GB-A 1,384,065. JP 6 116 125 OA; JP 0 516 323 1A; DE-A 1,950,101; DE-A 1,938,384; DE-A 2,532,722; DE-A 2,631,168; U.S. Pat. No. 3,853,936; FR-A 1,555,517; DE-A 2,933,601 and U.S. Pat. No. 3,549,504 disclose that isocyanates can be purified by special distillation and crystallization techniques. However, none of these methods achieves effective separation of troublesome chlorine compounds. These known methods are based on what is purely a physical treatment so only readily volatile chlorine compounds are separated. The use of methods of this type is thus restricted to particular isocyanate compounds, which are generally thermally stable and which are useful when a limited reduction in chlorine content is achieved.

Aside from treatment of isocyanate compounds by what are purely thermal techniques, treatments with additives have also been described in the literature. These treatments make it possible to achieve an improved separation of troublesome chlorine compounds. Patent specifications JP 4 501 032 9 B; JP 4 200 413 7 B; JP 5 908 845 2 A; JP 5 910 875 3 A; JP 5 917 245 0 A; U.S. Pat. No. 3,373,182; GB-A 1,111,581; U.S. Pat. No. 3,759,971; U.S. Pat. No. 4,094,894; ZA-A 8,100,606; DE-A 1,138,040; DE-A 1,286,025; U.S. Pat. No. 3,458,558; U.S. Pat. No. 3,264,336; SU-A 806 677 and DE-A 2,210,607 describe additives based on metals or alkali metals, such as metal oxides, metal cyanamides, metal hydrides or metal fatty acid esters for example, in the presence of sterically hindered phenols, metal naphthenates, metal silicates, alkali metal carbonates or organometallic compounds. These additives can only be separated with difficulty from the purified isocyanate, however, and result in unwanted contamination of the corresponding isocyanate product by metals or metal ions. Moreover, almost all metals and metal complexes cause an increase in the formation of byproducts (e.g., trimers, carbodiimides, dimer formation).

Similar restrictions apply to the use of additives such as imidazole (described in GB-A 1,347,647 and JP 0 505 898 2 A), sulfonic acids and esters thereof (described in GB-A 1,458,747), the acidic material described in U.S. Pat. No. 4,996,351, the diethyl sulfate (described in GB-A 1,459, 691), the sulfuric acid (also described in GB-A 1,459,691), epoxy compounds (DE-A 2,249,375; JP 0 932 396 8 A2), tetra-substituted ureas (DD 288 598), formic or acetic acid or derivatives thereof (U.S. Pat. No. 3,799,963) and the compounds having trimethylsilyl groups (described in EP-A 524 507). The use of organic bases or acids, particularly when these are employed for the purification of reactive isocyanate compounds, results in unwanted secondary reactions such as trimerization, dimer formation or carbodiimide formation.

Some compounds containing at least one Zerewitinoff-active NH group, such as ureas (DD 285 594), biurets (DD 288 597) or caprolactam (DD 285 593), as well as ammonium salts (DD 288 594), carbodiimides (DD 288 599), salts of primary and secondary amines (DD 288 593), tertiary alcohols and tertiary alkyl carbamates (DD 288 595) are recommended in the prior art for the purification of isocyanates. There are, however, disadvantages to using these materials also. For example, these additives need to be separated from the isocyanate or the usefulness of the isocyanate or distillation residue which contains the additive will be limited. Another particular disadvantage to use of these additives is the considerable reduction in NCO value which sometimes occurs, as well as the increase in viscosity which can result from the formation of biurets when tertiary alcohols are used. The last-mentioned disadvantage applies in particular when water is used to purify the isocyanate (DE-A 1,240,849; DE-A 1,240,849).

Patent Specification DD 288 596 describes low molecular weight alkyl phosphates as additives which are substantially inert to isocyanates and which, at temperatures of at least 200° C. and with the simultaneous use of inert gases, enable an effective reduction in the content of hydrolyzable chlorine to be achieved. In the examples given in this patent, temperatures of 225° C. for several hours are stated to be necessary for an effective reduction of the hydrolyzable chlorine content. These high temperatures, and the periods to which the products are exposed to them, restrict the use of this method to a few, relatively thermally stable isocyanates. Isocyanate compounds, particularly temperature-sensitive, low molecular weight isocyanates, are not stable when subjected to temperature/time conditions of this type, and decompose with the formation of carbodiimides and isocyanurates. This can result in an uncontrolled generation of process heat, which makes the reaction considerably more difficult to control. Moreover, the use of inert gas which is mandatory according to DD 288 596 inevitably results in a highly contaminated off-gas stream which has to be handled. Finally, it is difficult to separate the low molecular weight alkyl phosphates described above from the purified isocyanate, which is also of low molecular weight, by means of distillation or extraction.

SUMMARY OF THE INVENTION

It is an object of the present invention to provide a universally applicable method of purifying organic, low molecular weight isocyanates, particularly temperature-sensitive low molecular weight isocyanates, which does not possess the aforementioned shortcomings and which makes it possible to efficiently separate the product isocyanate from the reagents used for reducing the proportion of hydrolyzable chlorine.

These and other objects which will be apparent to those skilled in the art are accomplished by treating an isocyanate with a suitable amount of an additive corresponding to Formula (1). The required additive is added to the organic isocyanate(s) or mixture of isocyanates to be treated and the mixture is heated for a selected amount of time, optionally under increased or reduced pressure. Surprisingly, the method of the present invention permits the effective separation of troublesome chlorine compounds (reduction of the hydrolyzable chlorine content) at temperatures far below 200° C., without the mandatory use of inert gas.

DETAILED DESCRIPTION OF THE INVENTION

The present invention relates to a method for purifying low molecular weight isocyanates in which the low molecular weight isocyanate is treated with at least 0.1% by weight (based on weight of isocyanate) of a compound represented by the formula

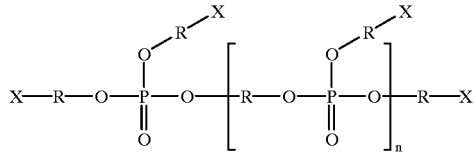

(1)

or with a mixture of compounds represented by Formula (1) in which n represents a number from 1 to 20 and each R independently represents linear or branched, saturated or unsaturated alkylene, cycloalkylene, aralkylene or bifunctional aryl radicals having from 1 to 20 carbon atoms, which may optionally include hetero atoms, such as oxygen, sulfur, silicon or nitrogen within their carbon chain and/or which may comprise oxygen, sulfur, or halogen atoms or nitrogen substituents, and/or which may contain other functional groups, and each X independently represents one of the following radicals:

H, OH. SH, O—$R^1$, S—$R^1$, O—Si($R^1$)$_3$, F, Cl, Br, I,

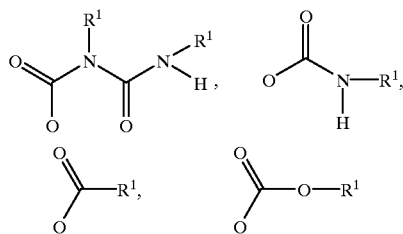

in which each $R^1$ independently represents an alkyl, cycloalkyl, aryl or aralkyl radical having from 1 to 20 carbon atoms, which may contain hetero atoms such as oxygen, sulfur, silicon or nitrogen, or $C_1$–$C_{20}$ alkylene, cycloalkylene, aralkylene or bifunctional aryl radicals, which may optionally contain hetero atoms such as oxygen, sulfur, silicon or nitrogen and may contain terminal functional groups such as NCO The isocyanate and compound represented by Formula (1) are heated, with or without an inert solvent which does not react with the isocyanate, for at least 10 minutes at a temperature of <200° C., and are subsequently freed, optionally by means of work-up by distillation or extraction, from high molecular weight compounds corresponding to Formula (1) and/or from high molecular weight reaction products.

The compounds represented by Formula (1) may be commercial products which may also still contain same terminal acidic functions, even though this is less preferred. Due to their method of production, compounds of Formula (1) comprise a polymer distribution which is random to a more or less pronounced extent, so that they may also contain small amounts of low molecular weight alkyl phosphates and other impurities.

Organic isocyanates which are purified by the method the present invention are suitable for the production of coatings, polyurethane moldings, and as intermediates.

The starting materials for the method of the present invention are low molecular weight isocyanates. As used herein, "low molecular weight isocyanates" include any mixtures of low molecular weight isocyanates. Examples of low molecular weight isocyanates of this type include:

a) monoisocyanates comprising aliphatically, cycloaliphatically, araliphatically or aromatically bonded isocyanate groups, such as butyl isocyanate, stearyl isocyanate, cyclohexyl isocyanate, benzyl isocyanate, 2-phenylethyl isocyanate, phenyl isocyanate and mixtures of monoisocyanates such as these;

b) diisocyanates which have molecular weights within the range of from about 140 g/mol to about 400 g/mol and which may comprise aliphatically, cycloaliphatically, araliphatically and/or aromatically bonded isocyanate groups, such as 1,4-diisocyanatobutane, 1,6-diisocyanatohexane (HDI), 2-methyl-1,5-diisocyanatopentane, 1,5-diisocyanato-2,2-dimethylpentane, 2,2,4- and 2,4,4-trimethyl-1,6-diisocyanatohexane, 1,10-diisocyanatodecane, 1,3- and 1,4-diisocyanatocyclohexane, 1,3- and 1,4-bis-(isocyanatomethyl)-cyclohexane, 1-isocyanato-3,3,5-trimethyl-5-isocyanatomethyl-cyclohexane (isophorone diisocyanate, IPDI), 4,4'-diisocyanatodicyclo-hexylmethane, 1-isocyanato-1-methyl-4(3) isocyanatomethyl-cyclohexane (IMCI), 2,4- and 2,6-diisocyanato-1-methylcyclohexane ($H_6$-

TDI), bis-(isocyanatomethyl)-norbornane, 2-methylpentane 2,4-diisocyanate, 1,3- and 1,4-bis-(2-isocyanatoprop-2-yl)-benzene (TMXDI), 2,4- and 2,6-diisocyanatotoluene (TDI), 2,4'- and 4,4'-diisocyanato-diphenylmethane, 1,5-diisocyanato-naphthalene, dipropylene glycol diisocyanate and any mixtures of diisocyanates such as these;

c) triisocyanates and/or isocyanates of higher functionality, such as 4-isocyanato-methyl-1,8-octane diisocyanate (nonane triisocyanate), 1,6,11-undecane triisocyanate and any mixtures of isocyanates such as these.

The starting materials for the method of the present invention may also comprise any mixtures of mono- and/or diisocyanates and/or triisocyanates and/or isocyanates of higher functionality.

In general, all organic isocyanates which have a molecular weight of up to about 400 g/mol, preferably from about 99 to about 279 g/mol, may be used as low molecular weight isocyanates in the present invention.

The aforementioned diisocyanates and isocyanates of higher functionality are preferably used in the method of the present invention. The use of 4-isocyanatomethyl-1,8-octane diisocyanate (nonane triisocyanate) is quite particularly preferred.

In the method of the present invention, the mixture of organic isocyanate and the compound corresponding to Formula (1) are heated with at least 0.1% by weight, preferably from about 0.5 to about 50% by weight, and most preferably from about 1.0 to about 5% by weight, based on the weight of isocyanate, for at least 10 minutes, preferably from about 1 hour to about 24 hours, most preferably from about 3 hours to about 15 hours, at a temperature of <200° C., preferably from about 140° C. to about 190° C. and most preferably from about 150° C. to about 180° C., with or preferably without an inert solvent which does not react with isocyanates. Optionally, thereafter, the purified, low molecular weight isocyanate may be freed, by distillation or extraction, from the high molecular weight compound corresponding to Formula (1) and/or from high molecular weight reaction products and from the inert solvents which do not react with isocyanates which may be present.

During or after heat treatment, the isocyanate may be removed by extraction or distillation, optionally under vacuum, from compounds of higher molecular weight. The purified isocyanate is preferably removed by distillation under vacuum (e.g. from 0.001 mbar to 100 mbar) from high molecular weight compounds corresponding to Formula (1) and/or from high molecular weight reaction products.

In order to prevent secondary reactions with air or with traces of moisture, the reaction apparatus can be operated under vacuum (for example from 100 to 1 mbar) or can be flushed with inert gas, for example nitrogen. In principle, however, the use of inert gas is not absolutely necessary.

The isocyanates which are obtained by the method of the present invention usually have hydrolyzable chlorine contents of <400 ppm, preferably of <250 ppm and most preferably of <150 ppm.

Before, during or after the chlorine content is reduced in accordance with the present invention, other methods of purification can also be used in order to remove color-imparting components and by-products, for example. These other methods of purification include treatments and/or whitening procedures using reducing agents or oxidizing agents and treatment with adsorbents such as activated carbon and/or hydrated silicas. Whitening procedures of this type can also exert a positive effect on the reduction of the chlorine content of the isocyanate compound.

Isocyanates which are purified in accordance with the present invention contain no harmful additions of metal compounds, acids, bases or other compounds which react with isocyanates, and preferably have a hydrolyzable chlorine content <250 ppm. They are capable of being used for a wide range of applications, e.g. for the production of oligomeric polyisocyanates or prepolymers, and in the case of triisocyanates can be used as starting materials for the production of intermediates, polyurethane moldings and coating media. Low molecular weight triisocyanates which are purified by the method of the present invention are preferably used as a hardener component in coatings.

Coating materials which contain isocyanates purified by the method of the present invention are suitable, in principle, for coating any substrates, such as wood, plastics, leather, paper, textiles, glass, ceramics, plaster, masonry, metals or concrete. They may be applied by any of the customary methods of application such as spraying, brushing, flooding, pouring, dipping or rolling. The coating materials can be used in the form of clear lacquers and can also be used in the form of pigmented lacquers, and are employed diluted in organic solvents or dispersed in water, or in undiluted form as a single- or multi-component coating.

EXAMPLES

The following Examples are given to illustrate the present invention. The values termed HC values which are given relate to the content of hydrolyzable chlorine. All percentages are given as percentages by weight.

100 g of the organic isocyanate specified in the Tables were mixed with the amount of compound A or B given in Tables 1 and 2 and were stirred under vacuum (10 to 100 mbar; depending on the isocyanate used) for the given period of time and temperature. After the given time of reaction, the products were subjected to work-up by thin film distillation (180° C./0.2 mbar). Products according to the invention were obtained in Examples 3, 4, 5, 7, 8, and 9.

TABLE 1

|  | Comparative Example 1 | Comparative Example 2* | Example 3 | Example 4 | Example 5 |
| --- | --- | --- | --- | --- | --- |
| Organic isocyanate | TIN$^1$ | TIN$^1$ | TIN$^1$ | TIN$^1$ | TIN$^1$ |
| additive used | — | triethyl phosphate | A | B | A |
| % by weight of additive | — | 2.5 | 2.5 | 2.5 | 10 |
| Temperature | 170° C. | 225° C. | 160° C. | 170° C. | 170° C. |
| Reaction time (hours) | 12 | 3 | 24 | 12 | 12 |

TABLE 1-continued

|  | Comparative Example 1 | Comparative Example 2* | Example 3 | Example 4 | Example 5 |
|---|---|---|---|---|---|
| HC value before treatment (ppm) | 5000 | 5000 | 5000 | 5000 | 5000 |
| HC value after treatment (ppm) | 1500 | <100 | <100 | <100 | <100 |
| NCO before heat treatment (ppm) | 47.1 | 44.7 | 46.0 | 46.0 | 46.0 |
| NCO after heat treatment (%) | 44.2 | 37.5 | 41.2 | 42.0 | 41.1 |

*Example 1 of DD 288 596
[1]Triisocyanatononane
Compound A: Exolit OP 550 (manufactured by Clariant) (OH number: 130; acid number <1, density: 1.31 g/cm³ at 25°, viscosity: about 2000 mPa · s)
Compound B: a reaction product formed from 1.0 equivalent of Exolit OP 550 (manufactured by Clariant) and 0.9 equivalent of butyl isocyanate.

The difference between the NCO contents before and after heat treatment provides information on unwanted secondary reactions and thus on any loss in yield.

In Comparative Example 2, which is not according to the invention, the conditions of Patent Specification DD 288 596 were reproduced in order to reduce the HC content of TIN. The clear reduction of NCO content indicates an unacceptably high level of contamination. Differential analysis indicated considerable, additional, uncontrolled evolution of heat from the reaction at this temperature (>600 kJ/kg), which would not be acceptable in an industrial process.

Even at 170° C. (Example 4), it was possible to reduce the HC content to less than 100 ppm under mild conditions, and at the same time only a slight reduction in NCO was ascertained.

TABLE 2

|  | Comparative Example 6 | Example 7 | Example 8 | Example 9 |
|---|---|---|---|---|
| Organic isocyanate | 4,4'-diiso-cyanato-diphenyl-methane | 4,4'-diiso-cyanato-diphenyl-methane | isophorone diisocyanate (IPDI) | hexa-methylene diisocyanate (HDI) |
| Additive used | — | B | B | B |
| % by weight of additive | — | 2.5 | 2.5 | 2.5 |
| Temperature | 170° C. | 170° C. | 170° C. | 170° C. |
| reaction time (hours) | 12 | 12 | 12 | 12 |
| HC value before treatment (ppm) | 391 | 391 | 156 | 48 |
| HC value after treatment (ppm) | 220 | 35 | 14 | 12 |
| NCO before heat treatment (%) | 31.3 | 30.6 | 36.9 | 48.8 |
| NCO after heat treatment (%) | 31.1 | 24.6 | 35.7 | 45.8 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for purifying a low molecular weight isocyanate comprising treating the low molecular weight isocyanate with at least 0.1% by weight, based on the weight of the isocyanate, of at least one high molecular weight compound represented by the following Formula (1)

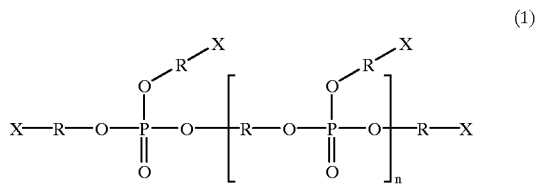

in which n represents a number frorm 1 to 20 and each R independently represents a linear or branched, saturated or unsaturated alkylene, cycloalkylene, aralkylene or bifunctional aryl radical having from 1 to 20 carbon atoms, which may optionally include hetero atoms within the carbon chain and/or which may comprise oxygen, sulfur, a halogen atom or a nitrogen substituent, and/or which may contain other functional groups, and each X independently represents one of the following radicals:

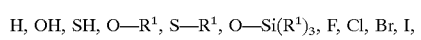

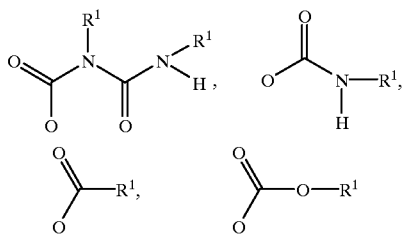

in which
- each R' independently represents an alkyl, cycloalkyl, aryl or aralkyl radical having from 1 to 20 carbon atoms, which may contain hetero atoms or a $C_1$–$C_{20}$ alkylene, cycloalkylene, aralkylene or bifunctional aryl radical which may optionally comprise hetero atoms and may have terminal functional groups for at least 10 minutes at a temperature of <200° C., and subsequently freeing the isocyanate from the at least one high molecular weight compound corresponding to Formula (1) and/or from high molecular weight reaction products, wherein the isocyanate purified comprises <250 ppm of hydrolyzable chlorine and wherein the isocyanate is freed from the high molecular weight compound represented by Formula (1) and/or high molecular weight reaction products by distillation or extraction.

2. The method of claim 1 in which the low molecular weight isocyanate is heated with from 1.0 to 5.0% by weight, based on the weight of the isocyanate, of the at least one high molecular weight compound represented by Formula (1) for from about 3 hours to about 15 hours at a temperature of from about 150 to about 180° C., and is subsequently distilled to free the isocyanate from the at least one high molecular weight compound represented by Formula (1) and/or high molecular weight reaction products.

3. The method of claim 1 in which 4-isocyanatomethyl-1,8-octane diisocyanate is the low molecular weight isocyanate.

* * * * *